United States Patent [19]

Schmidt

[11] Patent Number: 4,544,744
[45] Date of Patent: Oct. 1, 1985

[54] PROCESS FOR PREPARING 3,4,6-TRISUBSTITUTED 3-ALKYLTHIO-1,2,4-TRIAZIN-5-ONE DERIVATIVES

[75] Inventor: Thomas Schmidt, Haan, Fed. Rep. of Germany

[73] Assignee: Bayer Aktiengesellschaft, Leverkusen, Fed. Rep. of Germany

[21] Appl. No.: 666,420

[22] Filed: Oct. 30, 1984

[30] Foreign Application Priority Data

Nov. 4, 1983 [DE] Fed. Rep. of Germany ....... 3339859

[51] Int. Cl.[4] ........................................... C07D 253/06
[52] U.S. Cl. ................................................... 544/182
[58] Field of Search ......................................... 544/182

[56] References Cited

U.S. PATENT DOCUMENTS

| | | | |
|---|---|---|---|
| 4,309,538 | 1/1982 | Schmidt et al. | 544/182 |
| 4,315,094 | 2/1982 | Bonse et al. | 544/182 |
| 4,328,340 | 5/1982 | Bonse et al. | 544/182 |
| 4,408,044 | 10/1983 | Schmidt et al. | 544/182 |

Primary Examiner—John M. Ford
Attorney, Agent, or Firm—Sprung, Horn, Kramer & Woods

[57] ABSTRACT

A process for preparing a 3,4,6-trisubstituted 3-alkylthio-1,2,4-triazin-5-one of the formula

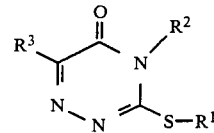

in which
$R^1$ is alkyl, alkenyl, alkynyl, optionally substituted cycloalkyl or optionally substituted aralkyl,
$R^2$ is amino, alkylamino or alkyl, and
$R^3$ is alkyl, halogenoalkyl, alkoxyalkyl, optionally substituted cycloalkyl, optionally substituted aryl or optionally substituted aralkyl, which comprises reacting a 3-mercapto-1,2,4-triazin-5-one of the formula

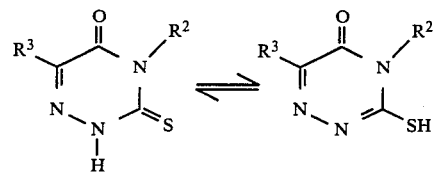

with an ester of an oxygen-containing acid as an alkylating agent, the reaction being effected at a temperature between about −20° and 180° C. in the presence of an at least equimolar amount of a strong oxygen-containing acid.

13 Claims, No Drawings

PROCESS FOR PREPARING 3,4,6-TRISUBSTITUTED 3-ALKYLTHIO-1,2,4-TRIAZIN-5-ONE DERIVATIVES

The present invention relates to a new industrially usable process for preparing largely known, herbicidally active 3,4,6-trisubstituted 3-alkylthio-1,2,4-triazin-5-one derivatives which involves alkylating the corresponding 3-mercapto derivatives in a highly acid medium.

It has already been disclosed that 3,4,6-trisubstituted 3-alkylthio-1,2,4-triazin-5-one derivatives of the formula (IA)

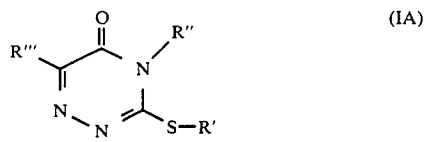

in which
R' represents alkyl, alkenyl, alkynyl, optionally substituted cycloalkyl or optionally substituted aralkyl,
R'' represents amino or alkyl and
R''' represents aliphatic, cycloaliphatic, aromatic, araliphatic or heterocyclic radicals which are all optionally substituted,
are obtained when corresponding 3-mercapto-1,2,4-triazin-5-one derivatives which can exist in two tautomeric forms and have the formula (IIA)

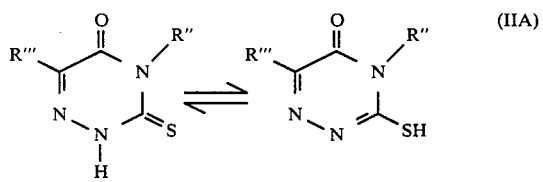

wherein
R'' and R''' have the abovementioned meaning, are reacted at temperatures between 0° and 50° C. in alkaline solution with alkylating agents of the formula (IIIA)

Hal—R'         (IIIA)

in which
Hal represents halogen and
R' has the abovementioned meaning, (compare A. Dornow et al., Chem. Ber. 97, pages 2173 to 8 (1964); and also for example DE-A-1 542 873, US-A-3 544 570 and US-A-3 671 523).

The expression "3-alkylthio-", according to the above definition of the R' radical, also embraces alkenylthio, alkynylthio, cycloalkylthio and aralkylthio radicals and some of their substitution derivatives; the same is true of the above expression "alkylating agents of the formula (IIIA)".

However, ths prior-disclosed process has a number of disadvantages. For instance, it requires large volumes of sodium hydroxide solution for dissolving the compounds of the formula (IIA), which leads to unfavorable spacetime yields. Furthermore, the appearance of halide, in particular bromide or iodide, is not unproblematical in the water pollution context, in particular in the case of an operation on an industrial scale. In many cases the use of alkylating agents of the formula (IIIA), such as, for example, methyl iodide or methyl bromide, leads to a not inconsiderable degree to undesirable alkylation of the nitrogen in the 2-position; the formation of these undesirable by-products, which lack herbicidal activity, must be regarded as the main disadvantage of the existing process. Methyl iodide, moreover, has the disadvantage of being a very costly alkylating agent, methyl bromide that of having a low boiling point, which leads to problems in industrial handling.

It has now been found, surprisingly, that the 3,4,6-trisubstituted 3-alkylthio-1,2,4-triazin-5-one derivatives of the formula (I)

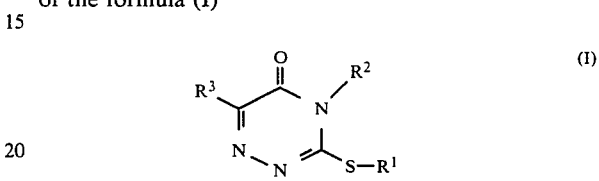

in which
$R^1$ represents alkyl, alkenyl, alkinyl, optionally substituted cycloalkyl or optionally substituted aralkyl,
$R^2$ represents amino, alkylamino or alkyl and
$R^3$ represents alkyl, halogenoalkyl, alkoxyalkyl, optionally substituted cycloalkyl, optionally substituted aryl or optionally substituted aralkyl,
are obtained in high yield and purity even on an industrial scale when 3-mercapto-1,2,4-triazin-5-one derivatives of the formula (II)

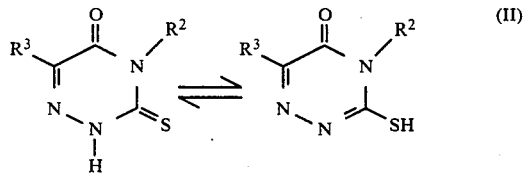

wherein
$R^2$ and $R^3$ have the abovementioned meaning, are alkylated at a temperature between −20° and 180° C., in the presence of an at least equimolar amount of a strong oxygen-containing acid, with oxygen acid esters which may also be produced in situ.

The expression "3-alkylthio-", according to the above definition of the $R^1$ radical, again also embraces alkyl derivatives, namely alkenylthio, alkynylthio, cycloalkylthio and aralkylthio radicals, and some of their substitution derivatives; the same is also true of the above expressions "alkylated", "alkylating agent" and "alkylation".

It must be regarded as very surprising that the 3,4,6-trisubstituted 3-alkylthio-1,2,4-triazin-5-one derivatives of the formula (I) are obtainable in high yield and purity by this process, because it was not foreseeable, on the one hand, how the starting compounds of the formula (II) would behave in a highly acidic medium, i.e. whether their rings might be cleaved or—especially if concentrated sulphuric acid was used—they might be involved in oxidation reactions, or whether protonation would take place, and if so in which position. Since the ring structure is left intact under the reaction conditions, it is indeed likely that protonation takes place in the highly acidic medium; whether just one or more intermediate products are formed is not known to date.

On the other hand, it was not possible to expect the compounds of the formula (II) still to be alkylatable once they had been protonated and even less that esters of oxygen acids would be highly suitable for this purpose. It is also surprising that the end products are stable under the strongly acid reaction conditions, in particular since in-house experiments have shown that compounds of the formula (I) tend to hydrolyse in dilute (for example 10% strength) aqueous acids.

The process according to the invention has the advantage of being technically simple to carry out and having a high space-time yield. The alkylating agents used do not cause waste water problems and are largely inexpensive substances. However, it is a particular advantage that the end products of the formula (I) are free of undesirable isomeric by-products alkylated at the nitrogen in the 2-position, which are inevitably produced with the prior-disclosed process.

The 3,4,6-trisubstituted 3-alkylthio-1,2,4-triazin-5-one derivatives preparable by the process according to the invention are defined in general terms by the formula (I), in which, preferably, $R^1$ represents straight-chain or branched alkyl having 1 to 12 carbon atoms, straight-chain or branched alkenyl having 2 to 6 carbon atoms, straight-chain or branched alkynyl having 2 to 6 carbon atoms, cycloalkyl having 5 to 7 carbon atoms which can be optionally monosubstituted to trisubstituted by identical or different substituents such as alkyl having 1 to 4 carbon atoms and halogen, or phenylalkyl which has 1 to 4 carbon atoms in the alkyl moiety and is optionally monosubstituted to trisubstituted by identical or different phenyl substituents such as halogen, alkyl having 1 to 4 carbon atoms, alkoxy and alkylthio each having 1 or 2 carbon atoms, nitro, cyano, halogenoalkyl, halogenoalkoxy and halogeno-alkylthio each having 1 or 2 carbon and 1 to 5 identical or different halogen atoms, optionally halogen-substituted phenyl and phenoxy;

$R^2$ represents amino, alkylamino having 1 to 4 carbon atoms or straight-chain or branched alkyl having 1 to 4 carbon atoms; and $R^3$ represents straight-chain or branched alkyl having 1 to 8 carbon atoms, halogenoalkyl having 1 to 8 carbon atoms and 1 to 4 identical or different halogen atoms, alkoxyalkyl having 1 to 4 carbon atoms in each alkyl moiety, cycloalkyl having 3 to 7 carbon atoms which is optionally monosubstituted to trisubstituted by identical or different substituents such as alkyl having 1 to 4 carbon atoms and halogen, or phenylalkyl having 1 to 4 carbon atoms in the alkyl moiety or phenyl which are each optionally monosubstituted to trisubstituted by identical or different phenyl substituents such as in each case preferably those already mentioned in the case of $R^1$.

In particularly preferred compounds of the formula (I), $R^1$ represents methyl or ethyl, $R^2$ represents amino, methylamino, methyl or ethyl, and $R^3$ represents straight-chain or branched alkyl having 1 to 6 carbon atoms, fluorine-, chlorine- or bromine-monosubstituted or -disubstituted tert.-butyl, methoxy- or ethoxy-monosubstituted or -disubstituted tert.-butyl, optionally identically or differently fluorine-, chlorine-, methyl- or ethyl-monosubstituted to -trisubstituted cycloalkyl having 3 to 7 carbon atoms, or phenylalkyl having 1 to 4 carbon atoms in the alkyl moiety or phenyl which are each optionally monosubstituted or disubstituted by identical or different phenyl substituents such as in each case fluorine, chlorine, bromine, methyl, methoxy, nitro, trifluoromethyl, trifluoromethoxy, phenyl and phenoxy.

If, for example, the starting materials used are 4-amino-3-mercapto-6-tert.-butyl-1,2,4-triazin-5-one and the strong oxygen-containing acid used is concentrated sulphuric acid, the course of the reaction in the process according to the invention can be represented by the following reaction equation:

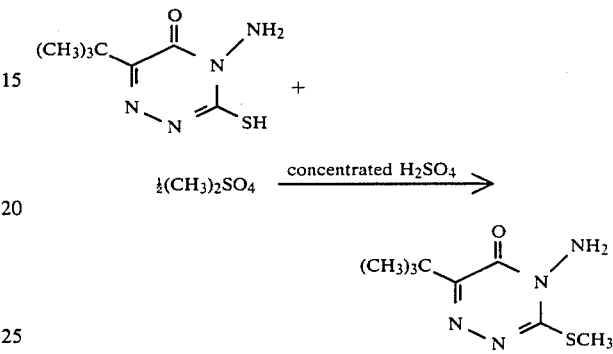

The 3-mercapto-1,2,4-triazin-5-one derivatives to be used as starting materials in carrying out the process according to the invention are defined in general terms by the above formula (II), in which $R^2$ and $R^3$ preferably represent those radicals which were already specified as preferable for these radicals in the context of describing the substances of the formula (I) which are preparable according to the invention.

The 3-mercapto-1,2,4-triazin-5-one derivatives of the formula (II) are known (compare for example US-A-3 671 523, US-A-3 544 570, EP-A-0 049 416, EP-A-0 074 538, EP-A-0 084 774, EP-A-0 058 885) and are obtainable in conventional manner using the methods given there.

The alkylating agents used can be the esters of any customary oxygen acid, which preferably includes the following compounds:

(a) monoesters and diesters of sulphuric acid of the formulae

and

in which $R^1$ has the abovementioned meaning; (b) monoesters, diesters and triesters of phosphoric acid of the formulae

and

and

in which $R^1$ has the abovementioned meaning;

(c) monoesters, diesters and triesters of phosphorous acid of the formulae $$R^1O-P(OH)_2 \quad (Va)$$

and $$(R^1O)_2P-OH \quad (Vb)$$

and $$(R^1O)_3P \quad (Vc)$$

in which
$R^1$ has the abovementioned meaning; (d) sulphonic acid esters of the formula $$R-SO_2OR^1 \quad (VI)$$

in which
$R^1$ has the abovementioned meaning and
R represents alkyl (in particular methyl), optionally substituted phenyl (in particular methylphenyl) or halogen (in particular chlorine);
(e) chlorocarbonic acid esters of the formula $$Cl-CO-OR^1 \quad (VII)$$

in which
$R^1$ has the abovementioned meaning; (f) chlorosulphinic acid esters of the formula $$Cl-SO-OR^1 \quad (VIII)$$

in which
$R^1$ has the abovementioned meaning;
(g) sulphinic acid esters of the formula $$R^1O-SO-OR^1 \quad (IX)$$

in which $R^1$ has the abovementioned meaning; (h) diesters of disulphuric acid of the formula $$R^1O-SO_2-O-SO_2-OR^1 \quad (X)$$

in which
$R^1$ has the abovementioned meaning; and (i) alkyl esters of highly acidic ion exchangers (particularly those containing sulphonic acid groups).

The oxygen acid esters of the formulae (III) to (X) are commonly known compounds of organic chemistry. They can be either put into the reaction as ready-made substance or be formed in situ from oxygen acids and for example alcohols, olefines, ethers, esters, epoxides, carbonates, urethanes or the like. The respective ways of forming the esters are well known reactions of organic and inorganic chemistry. Those alkyl esters of acidic ion exchangers mentioned under (i) are likewise known.

The reaction according to the invention is carried out in the presence of an at least equimolar amount of a strong oxygen-containing acid. This strong oxygen-containing acid can be any customarily usable strong inorganic or organic oxygen acid of $pK_a<2$, such as in particular sulphuric acid (including in the form of oleum), phosphoric acid, perchloric acid, methanesulphonic acid, methanedisulphonic acid, ethanesulphonic acid, chlorosulphonic acid, methylsulphuric acid, ethylsulphuric acid or monochloroacetic acid, dichloroacetic acid or trichloroacetic acid. The acids can be used in pure, concentrated form or diluted with a little water (while complying with the above $pK_a$), or even in the form of any mixtures with one another and to some extent even as a mixture with strong mineral acids which do not contain oxygen, such as, for example, hydrochloric acid; the glacial acetic acid/HCl mixture may be mentioned as an example from the last-mentioned group. Moreover, highly acidic ion exchangers—particularly those having sulphonic acid groups—can also be used instead of the acids mentioned.

The reaction temperatures can be varied within a relatively wide range in the course of carrying out the reaction according to the invention. The reaction is generally carried out—as specified above—between −20° and 180° C., preferably between 0° and 130° C., particularly preferably between 10° and 100° C.

The solvent or diluent for the reaction according to the invention is advantageously provided by using whichever strong oxygen-containing acid is used in excess. The reaction can, however, also be carried out in the presence of an inert organic solvent, for example when an acidic ion exchanger is used as the acid. Suitable solvents are hydrocarbons, such as, for example, benzene, toluene and gasoline fractions; chlorinated hydrocarbons, such as, for example, methylene chloride, chloroform, chlorobenzene and the dichlorobenzenes, and also nitroalkanes, such as, for example, nitromethane.

In carrying out the reaction according to the invention, 1 to 10 equivalents, preferably 1 to 5 equivalents, of alkylating agent and 1 to 30 moles, preferably 1 to 15 moles, of strong oxygen-containing acid are used per mole of 3-mercapto-1,2,4-triazin-5-one derivative of the formula (II). In the case of the diesters of sulphuric acid, sulphurous acid, disulphuric acid, phosphoric acid and phosphorous acid, 1 equivalent of alkylating agent corresponds to 0.5 mole of the diester, and in the case of the triesters of phosphoric acid sulphurous acid, disulphuric acid, and phosphorous acid, 1 equivalent of alkylating agent corresponds to 0.33 mole of the triester.

It should be emphasized that the process according to the invention can be carried out continuously or discontinuously, and the starting materials may be added in any order.

The reaction itself need not be allowed to proceed until all of the starting material has been converted. The reaction mixture can be worked up with organic solvents or with water.

There now follows a description of a particularly advantageous embodiment of the process according to the invention:

1 mole of 3-mercapto-1,2,4-triazin-5-one derivative of the formula (II) is suspended in 2 to 10 moles of 96% strength sulphuric acid, and 1.1 to 1.3 moles of an alcohol or an alkyl chlorosulphonate are added. The temperature is held at 10° to 100° C. for 2 to 5 hours, and the reaction mixture is hydrolyzed in water and neutralized, the end product of the formula (I) crystallizing out. The solid material is filtered off, washed with water and dried in vacuo.

In various cases it can, however, also be advantageous firstly to mix the alkylating agent with the sulphuric acid and only then to add the 3-mercapto-1,2,4-triazin-5-one derivative (II).

In some cases—if the reaction was carried out without an organic solvent—it will be found to be advantageous to add an organic solvent, such as, for example, petroleum ether or ligroin, to the reaction mixture before the end product is crystallized out, since any by-products are thereby held in solution.

The triazinone derivatives (I) preparable according to the invention are known to be distinguished by very powerful herbicidal activity (compare for example US-A-3 671 523, US-A-3 544 570, EP-A-0 049 416, EP-A-0 074 538, EP-A-0 084 774 and EP-A-0 058 885).

The process according to the invention is now illustrated in more detail by means of the following preparation examples.

PREPARATION EXAMPLES

EXAMPLE 1a

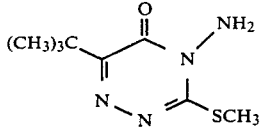

200 g (1 mole) of 4-amino-3-mercapto-6-tert.-butyl-1,2,4-triazin-5-one are dissolved in 300 g (about 3 moles) of 100% strength sulphuric acid, and 38.4 g (1.2 moles) of methanol are added. The mixture is heated at 80° C. for 4 hours, is discharged onto ice, is neutralized with sodium hydroxide solution, and is brought to pH 10.5–11.5. The resulting precipitate is filtered off, is washed with dilute sodium hydroxide solution and then with water until neutral, and is dried in vacuo at 50° C. This produces 171 g of 4-amino-3-methylthio-6-tert.-butyl-1,2,4-triazin-5-one (=94% of theory relative to consumed 4-amino-3-mercapto-6-tert.-butyl-1,2,4-triazin-5-one; conversion: 85%) having a melting point of 122° to 125° C.

The combined mother liquor is brought to pH 0.5–1 with acid; the precipitated, unreacted starting material is recovered by filtering and drying in vacuo at 50° C.

The end product is free of the 4-amino-2-methyl-3-thioxo-6-tert.-butyl-1,2,4-triazin-5-one isomer.

EXAMPLE 1b

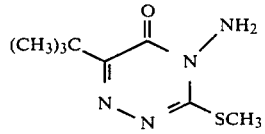

100 g (0.5 mole) of 4-amino-3-mercapto-6-tert.-butyl-1,2,4-triazin-5-one are dissolved in 250 g (about 2.5 moles) of 96% strength sulphuric acid, and 73 g (0.55 mole) of methyl chlorosulphonate are added. The mixture is reacted at 20°–30° C. for 4 hours, is then discharged onto ice, is neutralised with sodium hydroxide solution, and is brought to pH 10.5–11.5. The resulting precipitate is filtered off, is washed with dilute sodium hydroxide solution and then with water until neutral, and is dried in vacuo at 50° C. This produces 94.3 g of 4-amino-3-methylthio-6-tert.-butyl-1,2,4-triazin-5-one (=95% of theory relative to consumed 4-amino-3-mercapto-6-tert.-butyl-1,2,4-triazin-5-one; conversion: 95.1%) having a melting point of 122°–126° C.

The combined mother liquor is brought to pH 0.5–1 with acid; the precipitated, unreacted starting material is recovered by filtering and drying in vacuo at 50° C.

The end product is free of the 4-amino-2-methyl-3-thioxo-6-tert.-butyl-1,2,4-triazin-5-one isomer.

The following compounds of the general formula (I)

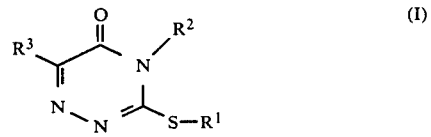

can be prepared in corresponding fashion under the stated process conditions:

TABLE 1

| Example No. | $R^1$ | $R^2$ | $R^3$ | Melting point (°C.) |
|---|---|---|---|---|
| 2 | $CH_3$ | $NH_2$ | $CH_3$ | 165 |
| 3 | $CH_3$ | $NH_2$ | $C_2H_5$ | 119–20 |
| 4 | $CH_3$ | $NH_2$ | $C_3H_7$—i | 123 |
| 5 | $CH_3$ | $NH_2$ | —$CH_2$—$CH(CH_3)_2$ | 65 |
| 6 | $CH_3$ | $NH_2$ | —$CH_2$—$C(CH_3)_3$ | 110–11 |
| 7 | $CH_3$ | $NH_2$ | —$CH(CH_3)$—$CH(CH_3)_2$ | 73–74 |
| 8 | $CH_3$ | $NH_2$ | —$CH(C_2H_5)_2$ | 53–57 |
| 9 | $CH_3$ | $NH_2$ | —$CH(CH_3)$—$CH_2CH(CH_3)_2$ | 71–75 |
| 10 | $CH_3$ | $NH_2$ | —$CH_2$—C$_6$H$_5$ | 166 |
| 11 | $CH_3$ | $NH_2$ | —$CH_2$—C$_6$H$_4$—Cl | 183 |
| 12 | $CH_3$ | $NH_2$ | —$CH_2$—C$_6$H$_4$—$OCH_3$ | 134–36 |
| 13 | $CH_3$ | $NH_2$ | —$C(CH_3)_2$—$CH_2F$ | 121–22 |
| 14 | $CH_3$ | $NH_2$ | —$C(CH_3)_2$—C$_6$H$_5$ | 119–29 |
| 15 | $CH_3$ | $NH_2$ | —$C(CH_3)_2$—$CH_2Cl$ | 98 |
| 16 | $CH_3$ | $NH_2$ | —$C(CH_2F)_2CH_3$ | 122–24 |
| 17 | $CH_3$ | $NH_2$ | —$C(CH_3)_2CH_2OCH_3$ | 74–76 |
| 18 | $CH_3$ | $NH_2$ | —$C(CH_3)_2$—C$_6$H$_4$—C$_6$H$_5$ | 180 |
| 19 | $CH_3$ | $NH_2$ | —$C(CH_3)_2$—$CH_2Br$ | 109–10 |
| 20 | $CH_3$ | $NH_2$ | —$C(CH_3)_2$—$CH_2OC_2H_5$ | $n_D^{20} = 1,534$ |
| 21 | $CH_3$ | $NH_2$ | —C$_6$H$_4$—Cl | 182 |
| 22 | $CH_3$ | $NH_2$ | —C$_6$H$_4$—$CH_3$ | 184–85 |
| 23 | $CH_3$ | $NH_2$ | —C$_6$H$_4$—F | 147 |
| 24 | $CH_3$ | $NH_2$ | —C$_6$H$_4$—$CF_3$ | 156 |

TABLE 1-continued

| Example No. | R¹ | R² | R³ | Melting point (°C.) |
|---|---|---|---|---|
| 25 | CH₃ | NH₂ |  cyclohexyl-H | 140-42 |
| 26 | CH₃ | NH₂ |  cycloheptyl-H | 152-54 |
| 27 | CH₃ | NH₂ |  phenyl | 188 |
| 28 | CH₃ | NH₂ | 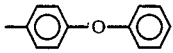 phenoxyphenyl | 185 |
| 29 | CH₃ | NH₂ |  CH₃-C(Cl)₂- | 133-34 |
| 30 | CH₃ | NH₂ |  2,4-difluorophenyl | 198-99 |
| 31 | CH₃ | NH₂ |  2-OCF₃-phenyl | 153-54 |
| 32 | CH₃ | NH₂ |  4-methylcyclohexyl | 117-19 |
| 33 | CH₃ | NH₂ |  cyclobutyl | 118-20 |
| 34 | C₂H₅ | NH₂ | —CH₂—C(CH₃)₃ | 105-11 |
| 35 | C₂H₅ | NH₂ | —CH(CH₃)—C₂H₅ | 74 |
| 36 | C₂H₅ | NH₂ | —CH₂—CH(CH₃)₂ | 79-81 |
| 37 | C₂H₅ | NH₂ | —C(CH₃)₂—CH₂F | 80-83 |
| 38 | C₂H₅ | NH₂ | —C(CH₂F)₂—CH₃ | 100-03 |
| 39 | C₂H₅ | NH₂ | —C(CH₃)₂—CH₂Cl | 93-96 |
| 40 | C₂H₅ | NH₂ | —(CH₃)₂—CH₂OC₂H₅ | 80-81 |
| 41 | C₂H₅ | NH₂ |  cyclobutyl | 140-41 |
| 42 | C₂H₅ | NH₂ | —C(CH₃)₂—CH₂OCH₃ | 83-84 |
| 43 | C₂H₅ | NH₂ | —CH(CH₃)₂ | 113-15 |
| 44 | C₂H₅ | NH₂ | —C(CH₃)₃ | 92-94 |
| 45 | CH₃ | CH₃ | CH₃ | 70 |
| 46 | CH₃ | CH₃ | —C(CH₃)₃ | 96 |
| 47 | CH₃ | CH₃ | —CH₂—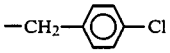—Cl | 140-42 |
| 48 | CH₃ | CH₃ | —C(CH₃)₂CH₂F | 102-04 |
| 49 | CH₃ | CH₃ | —CH₂—C(CH₃)₃ | 56-59 |
| 50 | CH₃ | CH₃ | —C(CH₃)₂—CH(CH₃)₂ | 103-04 |
| 51 | CH₃ | CH₃ | —C(CH₂F)₂—CH₃ | 104-07 |
| 52 | CH₃ | CH₃ |  cyclohexyl-H | 115 |
| 53 | CH₃ | CH₃ | 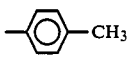 4-methylphenyl | 136-38 |
| 54 | CH₃ | CH₃ |  2-CF₃-phenyl | 125 |
| 55 | CH₃ | CH₃ |  2-chlorophenyl | 139 |
| 56 | CH₃ | CH₃ | 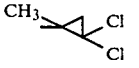 CH₃-C(Cl)₂- | 110-12 |
| 57 | CH₃ | CH₃ | 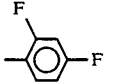 2,4-difluorophenyl | 117-19 |
| 58 | CH₃ | CH₃ | 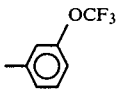 2-OCF₃-phenyl | 83-85 |
| 59 | CH₃ | CH₃ |  cyclopentyl-H | 72-73 |
| 60 | C₂H₅ | CH₃ |  phenyl | 69-71 |
| 61 | C₂H₅ | CH₃ |  cyclohexyl-H | 94-97 |
| 62 | C₂H₅ | CH₃ | —CH₂—CH(CH₃)₂ | 37-38 |
| 63 | C₂H₅ | CH₃ | —CH(CH₃)₂ | 70-74 |
| 64 | C₂H₅ | CH₃ |  cyclopentyl-H | 50-53 |
| 65 | C₂H₅ | CH₃ | —CH₂C(CH₃)₃ | 46-47 |
| 66 | C₂H₅ | CH₃ | —CH(CH₃)C₂H₅ | 48-49 |
| 67 | C₂H₅ | CH₃ | —C(CH₃)₂—CH₂F | 74-76 |
| 68 | C₂H₅ | CH₃ | —C(CH₂F)₂CH₃ | 102-04 |
| 69 | CH₃ | C₂H₅ | —CH₂—C(CH₃)₃ | 95-96 |
| 70 | CH₃ | C₂H₅ | —CH(CH₃)₂ | 79-81 |
| 71 | CH₃ | C₂H₅ | —C(CH₃)₂—CH₂F | 98-99 |
| 72 | CH₃ | C₂H₅ | —C(CH₂F)—CH₃ | 102-05 |
| 73 | CH₃ | C₂H₅ |  phenyl | 78 |
| 74 | CH₃ | C₂H₅ | 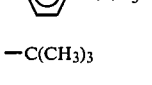 4-OCF₃-phenyl | 122-24 |
| 75 | C₂H₅ | C₂H₅ | —C(CH₃)₃ | 47 |
| 76 | CH₃ | NH₂ |  1-methylcyclobutyl | |
| 77 | CH₃ | NH₂ | —C(CH₃)₂—C₂H₅ | |
| 78 | CH₃ | NH₂ | cycloheptyl | |
| 79 | CH₃ | NH₂ |  1-methylcyclopentyl | |

TABLE 1-continued

| Example No. | R¹ | R² | R³ | Melting point (°C.) |
|---|---|---|---|---|
| 80 | CH₃ | NH₂ | 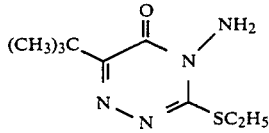 | |

EXAMPLE 44a

46 g (1 mole) of ethanol are added to 300 g (about 3 moles) of 100% strength sulphuric acid. The mixture is cooled to 20° C. and 200 g (1 mole) of 4-amino-3-mercapto-6-tert.-butyl-1,2,4-triazin-5-one are added. The reaction mixture is subsequently heated at 80° C. for 5 hours, is then poured onto ice, is neutralised with sodium hydroxide solution, and is brought to pH 10.5-11.5. The resulting precipitate is filtered off, is washed with dilute sodium hydroxide solution and then with water until neutral, and is dried in vacuo at 50° C. This produces 171.5 g of 4-amino-3-ethylthio-6-tert.-butyl-1,2,4-triazin-5-one ( 94.3% of theory relative to consumed 4-amino-3-mercapto-6-tert.-butyl-1,2,4-triazin-5-one; conversion: 79.75%) having a melting point of 93°-95° C.

The combined mother liquors are brought to pH 0.5 to 1 with acid; the precipitated, unreacted starting material is recovered by filtering and drying in vacuo at 50° C.

The end product is free of the 4-amino-2-ethyl-3-thioxo-6-tert.-butyl-1,2,4-triazin-5-one isomer.

It is understood that the specification and examples are illustrative but not limitative of the present invention and that other embodiments within the spirit and scope of the invention will suggest themselves to those skilled in the art.

I claim:

1. A process for preparing a 3,4,6-trisubstituted 3-alkylthio-1,2,4-triazin-5-one of the formula

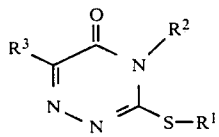

in which
$R^1$ is alkyl, alkenyl, alkynyl, optionally substituted cycloalkyl or optionally substituted aralkyl,
$R^2$ is amino, alkylamino or alkyl, and
$R^3$ is alkyl, halogenoalkyl, alkoxyalkyl, optionally substituted cycloalkyl, optionally substituted aryl or optionally substituted aralkyl,
which comprises reacting a 3-mercapto-1,2,4-triazin-5-one of the formula

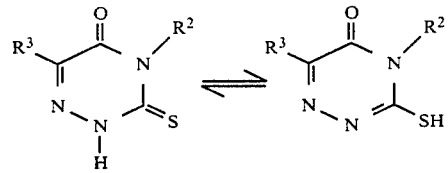

with an ester of an oxygen-containing acid as an alkylating agent, the reaction being effected at a temperature between about −20° and 180° C. in the presence of an at least equimolar amount of a strong oxygen-containing acid.

2. A process according to claim 1, wherein the reaction is effected at a temperature between about 0° and 130° C.

3. A process according to claim 1, wherein the reaction is effected at a temperature between about 10° and 100° C.

4. A process according to claim 1, wherein about 1 to 10 equivalents of the ester are employed per mole of triazinone.

5. A process according to claim 1, wherein the oxygen acid esters required as alkylating agent is produced in situ from the oxygen acid and an alcohol, olefin, ether, ester, epoxide, carbonate or urethane.

6. A process according to claim 1, wherein about 1 to 30 moles of the strong oxygen-containing acid are employed per mole of triazinone.

7. A process according to claim 1, wherein the strong oxygen-containing acid is of $pK_a < 2$.

8. A process according to claim 1, wherein the strong acid is at least one of sulphuric acid, phosphoric acid, perchloric acid, methanesulphonic acid, methanedisulphonic acid, ethanesulphonic acid, chlorosulphonic acid, methylsulphuric acid, ethylsulphuric acid, monochloroacetic acid, dichloroacetic acid, trichloroacetic acid or a highly acidic ion exchanger.

9. A process according to claim 1, wherein the strong oxygen-containing acid is a mixture of a strong oxygen-free mineral acid with an oxygen-containing acid of $pK_a < 2$.

10. A process according to claim 1, wherein the ester alkylating agent is selected from the group consisting of
(a) a monoester or diester of sulphuric acid of the formulae $$R^1O-SO_2-OH$$

and $$R^1O-SO_2-OR^1,$$

(b) a monoester, diester or triester of phosphoric acid of the formulae $$R^1O-PO(OH)_2,$$
$$(R^1O)_2PO-OH,$$

and $$(R^1O)_3PO,$$

(c) a monoester, diester or triester of phosphorous acid of the formulae $$R^1O-P(OH)_2,$$

$(R^1O)_2P\text{—}OH,$ and $(R^1O)_3P,$ (d) a sulphonic acid ester of the formula $R\text{—}SO_2OR^1$ in which
R is alkyl, optionally substituted phenyl or halogen,
(e) a chlorocarbonic acid ester of the formula $Cl\text{—}CO\text{—}OR^1,$ (f) a chlorosulphonic acid ester of the formula $Cl\text{—}SO\text{—}OR^1,$ (g) a sulphinic acid ester of the formula $R^1O\text{—}SO\text{—}OR^1,$ (h) a diester of disulphuric acid of the formula $R^1O\text{—}SO_2\text{—}O\text{—}SO_2\text{—}OR^1$, or (i) an alkyl ester of a highly acidic ion exchanger.

11. A process according to claim 1, in which
$R^1$ is $C_{1-12}$-alkyl, alkenyl or alkynyl having 2 to 6 carbon atoms, cycloalkyl having 5 to 7 carbon atoms optionally independently substituted up to three times by $C_{1-4}$-alkyl or halogen, or phenyl-$C_{1-4}$-alkyl optionally independently substituted by up to three times by halogen, $C_{1-4}$-alkyl, methoxy, ethoxy, methylthio, ethylthio, nitro, cyano, halogenoalkyl, halogenoalkoxy or halogeno-alkylthio each having 1 or 2 carbon atoms and up to 5 halogen atoms, phenyl, halophenyl, phenoxy or halophenoxy,
$R^2$ is amino, $C_{1-4}$-alkylamino or $C_{1-4}$-alkyl, and
$R^3$ is $C_{1-8}$-alkyl, $C_{1-8}$-halogenoalkyl having up to 4 halogen atoms, $C_{1-4}$-alkoxy-$C_{1-4}$-alkyl, $C_{3-7}$-cycloalkyl optionally independently substituted up to 3 times by $C_{1-4}$-alkyl or halogen, or phenyl-$C_{1-4}$-alkyl optionally substituted as in $R^1$.

12. A process according to claim 1, in which
$R^1$ is methyl or ethyl,
$R^2$ is amino, methylamino, methyl or ethyl, and
$R^3$ is $C_{1-6}$-alkyl, fluorine-, chlorine- or bromine-monosubstituted or di-substituted tert.-butyl, $C_{3-7}$-cycloalkyl optionally substituted up to 3 times by fluorine, chlorine, methyl and/or ethyl, or phenyl or phenyl-$C_{1-4}$-alkyl optionally substituted once or twice on the phenyl ring by fluorine, chlorine, bromine, methyl, methoxy, nitro, trifluoromethyl, trifluoromethoxy, phenyl and/or phenoxy.

13. A process according to claim 12, wherein the reaction is effected at a temperature between about 10° and 100° C., about 1 to 30 moles of the strong oxygen-containing acid are employed per mole of triazinone, the strong acid is at least one of sulphuric acid, phosphoric acid, perchloric acid, methanesulphonic acid, methanedisulphonic acid, ethanesulphonic acid, chlorosulphonic acid, methylsulphuric acid, ethylsulphuric acid, monochloroacetic acid, dichloroacetic acid, trichloroacetic acid or a highly acidic ion exchanger or a mixture of a strong oxygen-free mineral acid with an oxygen-containing acid of $pK_a<2$, and the alkylating agent is selected from the group consisting of (a) a monoester or diester of sulphuric acid of the formulae $R^1O\text{—}SO_2\text{—}OH$ and $R^1O\text{—}SO_2\text{—}OR^1,$ (b) a monoester, diester or triester of phosphoric acid of the formulae $R^1O\text{—}PO(OH)_2,$ $(R^1O)_2PO\text{—}OH,$ and $(R^1O)_3PO,$ (c) a monoester, diester or triester of phosphorous acid of the formulae $R^1O\text{—}P(OH)_2,$ $(R^1O)_2P\text{—}OH,$ and $(R^1O)_3P,$ (d) a sulphonic acid ester of the formula $R\text{—}SO_2OR^1$ in which
R is alkyl, optionally substituted phenyl or halogen,
(e) a chlorocarbonic acid ester of the formula $Cl\text{—}CO\text{—}OR^1,$ (f) a chlorosulphinic acid ester of the formula $Cl\text{—}SO\text{—}OR^1,$ (g) a sulphinic acid ester of the formula $R^1O\text{—}SO\text{—}OR^1,$ (h) a diester of disulphuric acid of the formula $R^1O\text{—}SO_2\text{—}O\text{—}SO_2\text{—}OR^1,$ or (i) an alkyl ester of a highly acidic ion exchanger.

* * * * *